US009993628B2

(12) United States Patent
Stigall et al.

(10) Patent No.: US 9,993,628 B2
(45) Date of Patent: Jun. 12, 2018

(54) BALLOON CATHETER JUNCTION (71) Applicant: Volcano Corporation, San Diego, CA (US)

(72) Inventors: Jeremy Stigall, Carlsbad, CA (US); Maritess Minas, San Diego, CA (US)

(73) Assignee: VOLCANO CORPORATION, San Diego, CA (US)

( * ) Notice: Subject to any disclaimer, the term of this patent is extended or adjusted under 35 U.S.C. 154(b) by 1331 days.

(21) Appl. No.: 13/972,352

(22) Filed: Aug. 21, 2013

(65) Prior Publication Data
US 2015/0057536 A1  Feb. 26, 2015

(51) Int. Cl.
A61M 29/00 (2006.01)
A61M 25/10 (2013.01)
A61B 8/12 (2006.01)
A61B 5/00 (2006.01)
A61B 8/00 (2006.01)

(52) U.S. Cl.
CPC ....... *A61M 25/1025* (2013.01); *A61B 5/0066* (2013.01); *A61B 5/0084* (2013.01); *A61B 8/12* (2013.01); *A61M 25/104* (2013.01); *A61M 25/1029* (2013.01); *A61M 25/1034* (2013.01); *A61B 8/445* (2013.01); *A61M 2025/1093* (2013.01); *Y10T 29/49826* (2015.01)

(58) Field of Classification Search
CPC ............. A61M 25/10; A61M 25/1025; A61M 25/104; A61M 25/1034; A61B 17/12109; A61B 2017/22001

USPC .......................................................... 606/194
See application file for complete search history.

(56) References Cited

U.S. PATENT DOCUMENTS

| | | | | |
|---|---|---|---|---|
| 5,156,594 A | * | 10/1992 | Keith | A61M 25/0662 604/103.09 |
| 5,810,869 A | | 9/1998 | Kaplan et al. | |
| 6,659,977 B2 | * | 12/2003 | Kastenhofer | A61M 25/00 604/264 |
| 2002/0032457 A1 | | 3/2002 | Sirhan et al. | |
| 2008/0249464 A1 | | 10/2008 | Spencer et al. | |
| 2010/0082012 A1 | | 4/2010 | Hattangadi et al. | |

FOREIGN PATENT DOCUMENTS

WO  WO 2012-0033936 A2  3/2012

OTHER PUBLICATIONS

International Search Report and Written Opinion received in Patent Cooperation Treaty Application No. PCT/US2013/055970, dated Dec. 9, 2013, 10 pages.

* cited by examiner

*Primary Examiner* — Melanie Tyson (57) ABSTRACT

A balloon catheter junction includes a distal junction on a distal end of a balloon. The junction includes an inner member, a balloon inner sleeve encompassing the inner member and bonded to an interior of a mid-shaft, and a balloon distal leg bonded to an exterior of the mid-shaft. A connection medium is disposed between the balloon inner sleeve and the inner member.

30 Claims, 7 Drawing Sheets

BALLOON CATHETER JUNCTION

CROSS-REFERENCE TO RELATED APPLICATIONS

The present application claims priority to and the benefit of U.S. Provisional Patent Application No. 61/692,193 filed Aug. 22, 2012, which is hereby incorporated by reference in its entirety.

TECHNICAL FIELD

Embodiments of the present disclosure relate generally to the field of medical devices and, more particularly, to integrated balloon sensing catheters.

BACKGROUND

Intravascular imaging systems are widely used in interventional cardiology as a diagnostic tool for a diseased vessel, such as an artery, within the human body. Various sensors may be placed on a catheter and positioned in the body. One type of imaging system is an intravascular ultrasound (IVUS) system. In one example, a phased array IVUS device includes a number of transducers that are passed into a vessel and guided to an area to be imaged. The transducers emit ultrasonic waves in order to create an image of the vessel of interest. The ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Intravascular imaging systems are often used to detect arterial occlusions that can be relieved through use of a balloon catheter. A balloon catheter is a type of catheter with a balloon near the tip. The balloon catheter is designed to be inserted into a patient's artery and positioned to a spot where an occlusion was detected through use of an intravascular imaging system. Upon reaching the detected occlusion, the balloon is inflated to relieve the occlusion.

An intravascular imaging system may be integrated at the distal end of a balloon catheter. With such integration, the intravascular imaging system does not have to be first removed from the patient's artery before the balloon can be used to relieve the occlusion. Rather, upon detection of an occlusion, the catheter can be pushed further into the patient so that the balloon is aligned with the occlusion.

SUMMARY

In one embodiment, a balloon catheter includes a distal junction on a distal end of a balloon. The distal junction includes an inner member, a balloon inner sleeve encompassing the inner member and bonded to an interior of a mid-shaft, and a balloon distal leg bonded to an exterior of the mid-shaft. A connection medium is disposed between the balloon inner sleeve and the inner member.

In another embodiment, a therapeutic catheter includes an inner member surrounded by an inner sleeve. The catheter also includes a connection medium within a space between the inner member and the inner sleeve, the connection medium connecting a sensing device at a distal end of a treating device to circuitry at a proximal end of the treating device. The inner sleeve is bonded to a distal shaft at a distal end of the treating device and a proximal shaft at a proximal end of the treating device.

In another embodiment, a balloon catheter includes a proximal junction and a distal junction. The proximal junction includes an inner member, a balloon inner sleeve encompassing the inner member and bonded to an interior of a proximal shaft, and a balloon proximal leg bonded to an exterior of the proximal shaft. The distal junction includes a mid-shaft, an interior of the mid-shaft bonded to the balloon inner sleeve, and a balloon distal leg bonded to an exterior of the mid-shaft. A connection medium is disposed between the balloon inner sleeve and the inner member.

In another embodiment, a method for using a therapeutic catheter within a patient includes inserting a tip of a catheter into a patient, the catheter designed to follow a guide-wire, the tip comprising a sensing device. The method further includes continuing to insert the catheter into the patient along the guide-wire so that a distal end of a balloon enters the patient, a junction at the distal end comprising an inner member, a balloon inner sleeve encompassing the inner member and bonded to an interior of a mid-shaft, and a balloon distal leg bonded to an exterior of the mid-shaft. The method further includes continuing to insert the catheter into the patient along the guide-wire so that a proximal end of the balloon enters the patient, a junction at the proximal end that includes a proximal shaft, an interior of the proximal shaft bonded to the balloon inner sleeve, and a balloon proximal leg bonded to an exterior of the proximal shaft, the connection medium being disposed between the balloon inner sleeve and the inner member.

In another embodiment, a method for fabricating a sensing balloon catheter includes joining a distal end of a balloon inner sleeve to an interior of a mid-shaft, the balloon inner sleeve encompassing an inner member. The method further includes joining a proximal end of the balloon inner sleeve to a proximal shaft, and mounting a sensor having a connection medium extending proximally therefrom in a connection medium within a space between said balloon inner sleeve and said inner member.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

Figure 1:
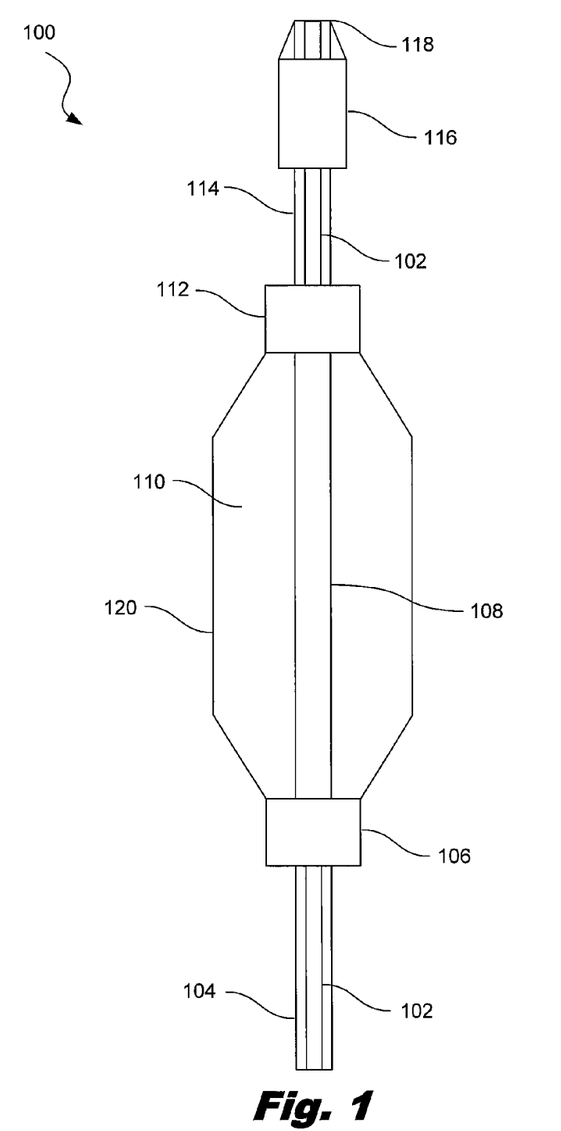
FIG. 1 is a diagram showing an illustrative sensing catheter, according to one example of principles described herein.

FIG. 1 is a diagram showing an illustrative balloon catheter 100. According to certain illustrative examples, the catheter 100 includes a balloon assembly 110 with an outer sleeve 120 and an inner sleeve 108. The balloon assembly 110 is joined to a proximal shaft 104 through a proximal junction 106. Additionally, the balloon assembly 110 is joined to a mid-shaft 114 through a distal junction 112. In the illustrated embodiment, the mid-shaft 114 extends between the balloon assembly 110 and a sensing device 116. An inner member 102 defining a guide wire lumen 103 runs from the tip 118 of the catheter, through the interior of the proximal shaft 104, the balloon assembly 110, and the mid-shaft 114, to at least the proximal end of the balloon assembly 110.

The proximal shaft 104 connects the balloon assembly 110 to a pressurized fluid system while connection medium 208, such as electrical conductors or optical fibers, extending within the proximal shaft connect the sensor 116 to a processing systems (not shown) at the proximal end of the catheter 100. In one aspect, the sensor 116 is an ultrasound transducer array having a maximum outer diameter of 3.5 F and the connection medium 208 is a microcable having a braided exterior with 7 individual insulated electrical conductors. The processing systems typically remain outside of the patient. The processing system uses the data received from the sensing device 116. When the sensor is part of an imaging system, the data can be used to create an image. The image can be displayed to a medical professional in real time as the catheter moves through the patient's artery. This allows the medical professional to find various occlusions or other irregularities which may exist throughout the patient's artery. In a similar manner, the sensor could be a pressure or flow sensor, and the processing system could determine fractional flow reserve values based on the sensed data.

The proximal shaft 104 is made of a plastic, polymer, or other flexible material. The proximal shaft 104 is designed to be flexible so that it may effectively traverse a patient's artery without damaging the artery. The proximal shaft 104 may be a dual lumen shaft. The dual lumen proximal shaft 104 may be an axial dual lumen shaft with an inner lumen and an outer lumen.

The proximal shaft 104 may have a diameter within the range of 2-4 French. The length of the proximal shaft 104 is long enough to allow the balloon 110 and the sensing device 116 to reach a sufficiently deep region of a patient's artery. For example, the proximal shaft 104 may have a length of approximately 150 cm. In a collapsed condition, the maximum outer diameter of the balloon assembly is approximately 0.040 inches.

Figure 5A:
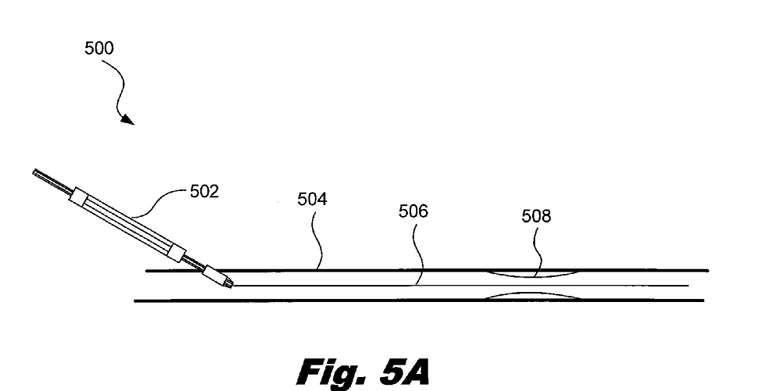
FIGS. 5A-5C are diagrams showing an illustrative insertion of a balloon catheter into a patient, according to one example of principles described herein.

The inner member 102 defines a guidewire lumen 103 that is sized to receive a guide-wire (shown in FIG. 5A). In one embodiment, the guidewire lumen has a diameter of 0.017 inches such that it can receive a 0.014 inch diameter guidewire. Typically, a guide-wire is first inserted into a patient's artery. The catheter is then placed over the guide-wire such that the inner member 102 encompasses the guide-wire. In some examples, the inner member 102 may extend the entire length of the catheter 100, from the tip 118 to the proximal end of the proximal shaft 104. Such a catheter is referred to as an over-the-wire catheter. In some examples, the inner member 102 may extend along a short distance and then exit out of the catheter at an exit port near the proximal end of the balloon 110. Such a catheter is referred to as a rapid exchange catheter.

The length of the inner member is long enough to extend from the point at which the catheter starts on the guide-wire (typically, the tip) to the point at which the guide-wire exits the catheter. Thus, the length may be relatively short in the case of a rapid exchange catheter and relatively long in the case of an over-the-wire catheter.

The mid-shaft 114 is connected between the distal end of the balloon 110 and the sensing device 116. The mid-shaft 114 is made of a polymer, plastic, or other flexible material. The mid-shaft 114 is flexible so that it may effectively traverse a patient's artery without damaging the artery. The inner member 102 runs through the interior of the mid-shaft 114. Additionally, a connection medium runs from the sensing device 116 towards the balloon 110 through the mid-shaft 114.

Figure 2:
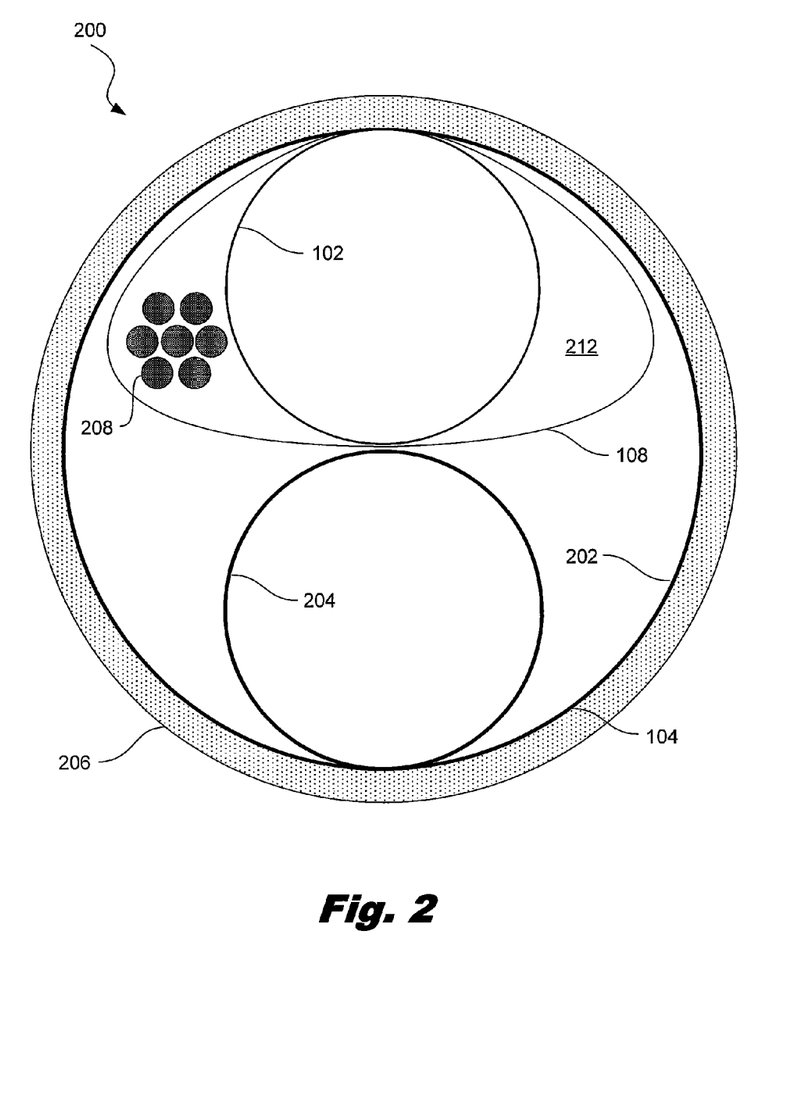
FIG. 2 is a diagram showing an illustrative cross-section taken along line 2-2 of FIG. 1 of a proximal junction of a balloon catheter, according to one example of principles described herein.

FIG. 2 is a diagram showing an illustrative cross-section of a proximal junction 106 of a balloon catheter. The proximal junction 106 connects the proximal end of the balloon to the proximal shaft (e.g., 104, FIG. 1). According to certain illustrative examples, the proximal shaft is a dual lumen shaft that includes an inner lumen 202 and an outer lumen 204. The proximal junction 106 also includes the inner member 102, the inner balloon sleeve 108, and a space through which connection media 208 run. The proximal junction 106 further includes a balloon proximal leg 206. In one aspect, the balloon proximal leg 206 is an extension of the material forming the balloon outer sleeve 120.

The outer lumen 202 of the proximal shaft 104 provides an external structure for the proximal shaft 104. The inner lumen 204 is smaller in diameter than the outer lumen 202 and runs axially within the outer lumen 202. The size of the inner lumen 204 is such that there is sufficient room within the outer lumen for the inner member 102, inner balloon sleeve 108, and connection media 208.

The inner lumen 204 can be used to pump inflation fluid into the balloon. Thus, the end of the inner lumen 204 within the proximal junction 200 serves as an inflation port where the inflation fluid exits the inner lumen 204 into the balloon. The inflation fluid exits into the space between the balloon inner sleeve 108 and the balloon outer sleeve, thus inflating the balloon.

The balloon inner sleeve 108 acts as a barrier between the inflation fluid and any structures that run through the internal portion of the catheter, particularly, the connection media 208 and the inner member 102. The balloon inner sleeve 108 is bonded to the interior of the outer lumen 202 of the proximal shaft 104. Additionally the balloon inner sleeve 108 encompasses the inner member 102. As shown more fully in FIG. 3, the balloon inner sleeve 108 is sized such that there is sufficient space 212 between the sleeve 108 and the inner member 102 so as to allow any connection media 208 to fit therein. This space 212 allows the connection media 208 to float freely without damaging the integrity of the balloon. However, bonding material 213 fills the space in the proximal connection 106 and distal connection 112 to define a fluid tight region 212 within inner sleeve 108 beneath balloon 120. In one aspect, the inner sleeve is formed of a multi-layer structure suitable for high pressure operation greater than 10 atmospheres (ATM), although in manner applications operating pressures may extend into a range of 15 to 20 ATM. The material properties and construction of the inner sleeve allow it to deform under high pressure without significant elongation along the longitudinal axis of the balloon assembly. The materials permit very little, if any, axial compression and extension. In one embodiment, the inner sleeve is formed by an inner layer of polyethylene bonded to an outer layer of maleated polyethylene. The outer layer of maleated PE is more suitable for heat treated bonding to other components of the system, such as the proximal shaft 104 and mid-shaft 114, that can be formed of PBAX. It will be understood that the proximal shaft 104, mid-shaft 114 and inner shaft 102 are formed such that they do not deform under the high operating pressures while inner sleeve 108 is designed to intentionally elastically deform inwardly under the high operating pressures of the balloon system. The inner sleeve 108 then elastically returns to its original shape when the high pressure condition is removed. Return of the inner sleeve to its original shape may also be aided by the compressed gas within the space 212.

Various types of connection media may run through the space 212 between the inner member 102 and the balloon inner sleeve 108. For example, in the case that the sensing device produces electrical signals to be processed by external systems, then the connection media may include conductive wires to carry those electrical signals. Alternatively, the connection media may include fiber optic cables to propagate those signals in the form of light. The number of wires or cables depends on the type of sensing device and the manner in which data is transferred from the sensing device to the external processing systems. Conductive wires may also be used to provide electrical power to the sensing device.

In the case that the sensing device is rotational, the connection media 208 may include a driveshaft lumen. The driveshaft lumen includes a plastic sheath filled with a liquid lubricant. The lubricant allows the driveshaft running through the plastic sheath to spin with a minimal amount of friction against the interior of the plastic sheath. This prevents the sheath from spinning with the proximal shaft 104, which could result in damage to a patient's artery.

The balloon proximal leg 206 is part of the balloon outer sleeve (e.g., 120, FIG. 1). The balloon proximal leg 206 is designed to fit securely around the exterior of the proximal shaft 104. The balloon proximal leg 206 may be bonded to the exterior of the proximal shaft through a variety of bonding methods. These bonding methods include, but are not limited to, thermal bonding and laser bonding.

Figure 3:
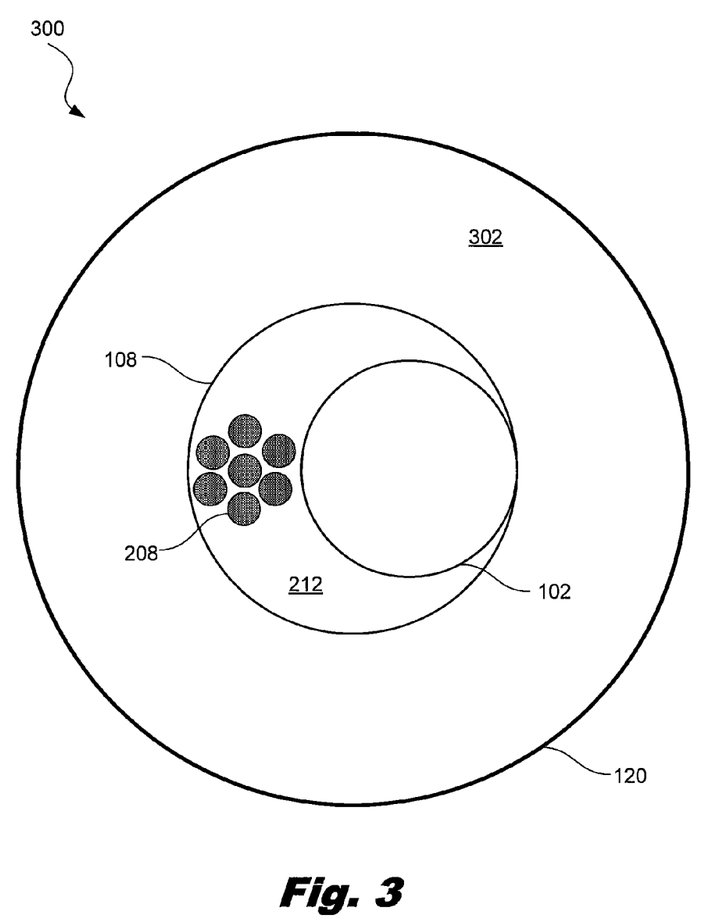
FIG. 3 is a diagram showing an illustrative cross-section of a balloon taken along line 3-3 of FIG. 1, according to one example of principles described herein.

FIG. 3 is a diagram showing an illustrative cross-section of a balloon assembly 110 taken along line 3-3 of FIG. 1. According to certain illustrative examples, the cross-section includes the balloon outer sleeve 120, the balloon inner sleeve 108, the connection media 208, and the inner member 102. The diameter of the balloon depends on the amount of inflation fluid 302 pumped into the balloon through the proximal junction. For non-distensible balloon materials, the balloon diameter is fixed to a specific diameter. In one embodiment, the non-compliant balloon has a working length of approximately 15 mm and is available in expanded diameters ranging from 2.0 to 4.0 mm in 0.5 mm increments.

In one embodiment, the outer diameter of the balloon assembly in the collapsed state is approximately 0.040 inches.

The proximal shaft at the proximal end of the balloon and the mid-shaft at the distal end of the balloon are independent shafts. According to certain illustrative examples, there is not a continuous shaft extending through the interior of the balloon. Rather, the interior of the balloon includes only the connection media 208 and the inner member 102. This provides additional flexibility within the balloon. Moreover, this allows the connection media 208 to float freely within the space 212 between the balloon inner sleeve 108 and the inner member 102. In the illustrated example, the ends of the inner sleeve 108 are sealed to the respective proximal and distal catheter components forming a fluid tight chamber 212 surrounding microcable 208 and inner member 102. In some cases, the space 212 may be filled with air or other gases, while in some cases the space 212 may be filled with a liquid.

As mentioned above, an inflation fluid is used to inflate the balloon when it is appropriately aligned in order to perform various medical tasks such as relieving an arterial occlusion. Thus, the diameter of the balloon outer sleeve 120 changes based on the inflation status of the balloon. As the balloon is non-compliant, the diameter only extends to a certain point. The non-compliant nature of the balloon prevents too much expansion within a patient's artery. The balloon inner sleeve 108 is designed with an integrity such that the balloon inner sleeve 108 will not place too great of a pressure on the connection media 208 when the balloon is inflated.

Figure 4:
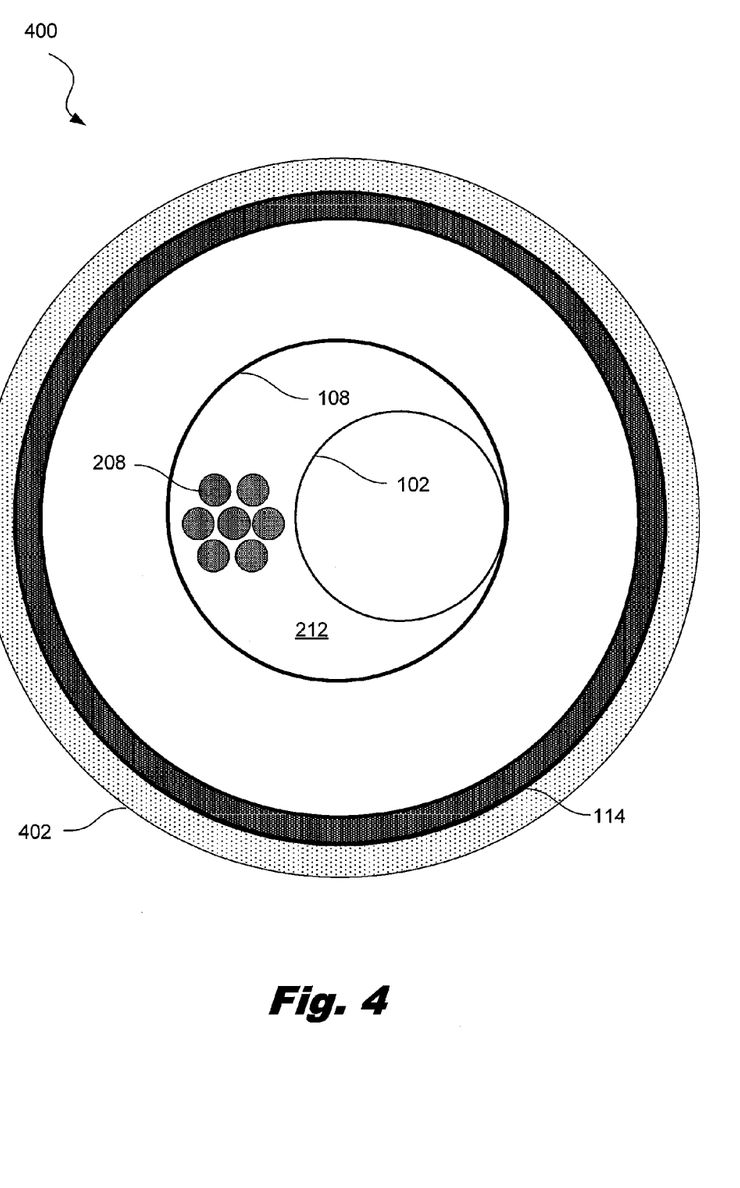
FIG. 4 is a diagram showing an illustrative cross-section of a distal junction of a balloon catheter taken along line 4-4 of FIG. 1, according to one example of principles described herein.

FIG. 4 is a diagram showing an illustrative cross-section of a distal junction 400 of a balloon catheter. According to certain illustrative examples, the distal junction 400 connects the balloon to a mid-shaft 114 at the distal end of the balloon. The distal junction 400 also includes the inner member 102, the inner balloon sleeve 108, and a space 212 through which connection media 208 runs. The distal junction 400 further includes a balloon distal leg 402.

The mid-shaft 114 is an independent shaft that is connected adjacent its proximal end to the distal end of the balloon and adjacent its distal end to the sensing device. The mid-shaft 114 is also designed to be flexible in order to allow the catheter to effectively traverse a patient's artery. The mid-shaft 114 may have a diameter within the range of 2.5 to 4 French.

The length of the mid-shaft depends on the desired distance between the distal end of the balloon and the sensing device. The length may be long enough so that the sensing device does not interfere with the distal junction as the catheter traverses sharper turns. The length of the mid-shaft may also be short enough so as not to push the sensing device too much deeper into the patient's artery when using the balloon to relieve an arterial occlusion. In one example, the length of the mid-shaft may be a length within a range of 3 to 15 mm with an exemplary range from 5 to 10 mm in length.

The balloon inner sleeve 108 is bonded to the interior of the mid-shaft 114. Additionally, the exterior of the mid-shaft 114 is bonded to the balloon distal leg 402. The balloon distal leg 402 is part of the balloon outer sleeve and is designed to fit securely around the mid-shaft 114. Because the mid-shaft is independent from the proximal shaft, the integrated catheter has an overall greater flexibility. Additionally, the connection media 208 are allowed to float freely through the center of the balloon without comprising the integrity of the balloon. In one aspect, the connection medium 208 comprises a braided microcable having seven individually insulated electrical conductors. In the illustrated embodiment of FIG. 3, the external braid material has been removed so that each conductor can float independently within the space 212 defined within inner sleeve 108. It will be appreciated that the during the bonding process, the individual conductors will have some slack between the distal and proximal bonding areas such that the conductors can be curved to follow tortuous vessel paths and can migrate over one another under high pressure balloon inflation. The relatively free movement of the conductors within the balloon assembly provides a low profile and highly flexible assembly that inhibits conductor breakage while providing a fluid tight inflation system for high pressure capabilities above 20 ATM.

As mentioned above, the balloon 120 can be used to relieve various types of arterial occlusions. When the balloon 120 is appropriately positioned within a patient's artery, the balloon 120 is then inflated to put pressure on the occlusion. The balloon 120 is typically inflated with an inflation fluid. The inflation fluid is typically a saline fluid as such a fluid is harmless to the patient if it leaks into the artery. The inflation fluid may be pumped into the balloon through an inner lumen of the proximal shaft 104 to a range of 15 to 20 ATM, or even greater depending on material properties of the balloon.

According to certain illustrative examples, the balloon 120 is a non-compliant balloon. A non-compliant balloon is one that is designed to inflate to a particular diameter and not stretch beyond that diameter. This prevents the balloon 120 from expanding too much. This is important because excess expansion could damage a patient's artery. The balloon 120 may also be designed to resist too much axial compression, which could allow the non-compliant balloon 120 to expand farther than desired. Additionally, the balloon 120 may be designed to resist too much axial stretching, which could prevent the balloon 120 from expanding to the desired diameter. In one further example, a stent is positioned in a compressed state around the balloon for delivery to a site of stenosis. The balloon may be inflated to plastically expand the stent to open the vessel and the stent can remain in a supporting position after the balloon is deflated.

As mentioned above, the sensing device 116 can be used to image the interior of a patient's artery. Various types of sensing devices may be used. One example of a sensing device 116 is an optical coherence tomography (OCT) device. In another form, the sensor can collect information for spectroscopy or photo acoustic imaging. The sensing device 116 may also be a forward looking device that scans forward into the artery rather than outward from the axis towards the arterial walls.

The sensing device 116 may also be an IVUS device. There are two general types of IVUS devices that may be used. The first type of device is a solid state device, also known as a phased array. Solid-state IVUS devices carry a transducer complex that includes an array of ultrasound transducers distributed around the circumference of the device. The transducers are connected to a set of transducer controllers. The transducer controllers select individual transducers for transmitting an ultrasound pulse and for receiving the echo signal. By stepping through a sequence of transmit-receive pairs, the solid-state IVUS system can synthesize the effect of a mechanically scanned transducer element, but without moving parts. Because there is no rotating mechanical element, the transducer array can be placed in direct contact with the blood and vessel tissue with minimal risk of vessel trauma. Furthermore, the interface is simplified because there is no rotating element. The solid-state scanner can be wired directly to the imaging system with a simple electrical cable and a standard detachable electrical connector.

In the example of a transducer array as a sensing device, the connection medium running through the catheter shafts includes the electrical cables that communicate data between the transducer array and external processing systems. The number of wires and cables comprising the connection media may depend on the type of transducer array. For example, a 64 bit array may use more cables than a 32 bit array. Additionally, various multiplexing functions may be used to reduce the number of wires running through the catheter shafts.

The second general type of IVUS device is a rotational device. A typical rotational IVUS device includes a single ultrasound transducer element located at the tip of a flexible driveshaft. In one aspect, the transducer is positioned distally of the balloon while in another embodiment the transducer is positioned within the inner sleeve 108 within the balloon assembly. The driveshaft spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

In the example of a rotational array as a sensing device 116, the connection media running through the catheter shafts includes a driveshaft lumen that comprises the plastic sheath surrounding a driveshaft used to drive the rotational array. Additionally, the connection media include any electrical cables that communicate data between the transducer array and external processing systems.

Figure 5B:
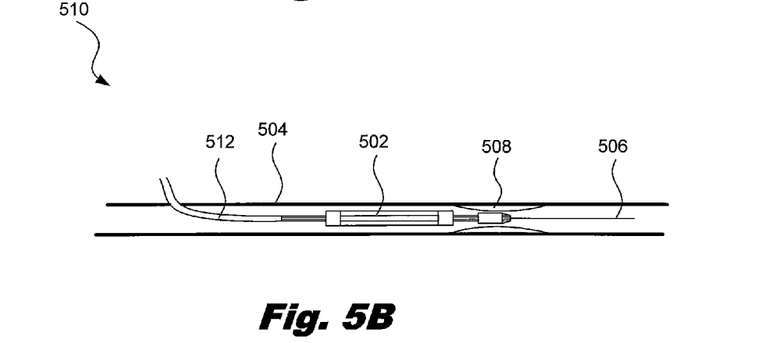
Figure 5C:
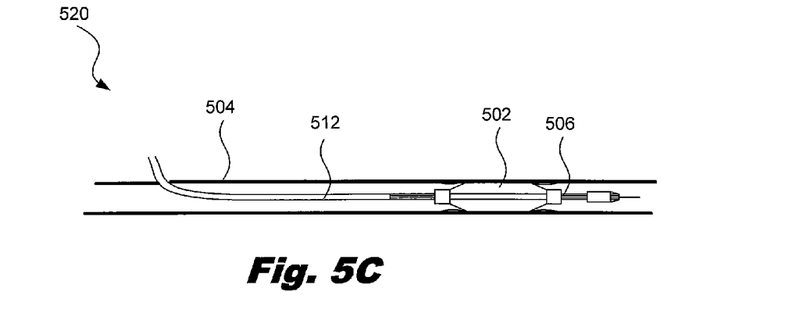

FIGS. 5A-5C are diagrams showing an illustrative insertion of a balloon catheter into a patient. According to certain illustrative examples, a guide-wire 506 is fed into a patient's artery 504. In one aspect, a guidewire having a diameter of approximately 0.014 inches can be utilized. The catheter can then be moved along that guide-wire 506 deeper into the patient's artery 504.

FIG. 5A is a diagram 500 showing an integrated catheter being pushed into a patient's artery 504. The tip of the catheter 502 can be designed to facilitate such entry. Although not shown, it will be understood that in some applications a guiding catheter having a minimum internal diameter of approximately 6 French (0.066 inches) may be used to facilitate placement of the sensing balloon catheter. At this point, the balloon is not inflated. The catheter is pushed into the artery 504 until the distal junction of the balloon enters the artery 504. The catheter 502 is then pushed further into until the proximal junction enters the artery 504. Thereafter, the catheter 502 is pushed further into the artery with the proximal shaft 512 extending outside the artery 504 and outside the patient.

FIG. 5B is a diagram 510 showing the catheter 502 moving through the patient's artery. According to certain illustrative examples, the catheter 502 traverses the artery 504 as a doctor views the data obtained by the sensing device. This data will inform the doctor if there is some type of arterial occlusion 508. Upon finding such an occlusion 508, the catheter 502 is pushed further into the patient a known distance such that the balloon is aligned with the occlusion 508.

FIG. 5C is a diagram 520 showing the integrated balloon catheter 502 inflated in order to relieve an arterial occlusion. According to certain illustrative examples, upon being appropriately aligned, the balloon is inflated in order to relieve the occlusion. As mentioned above, this is done by pumping an inflation fluid through an inner lumen of the proximal shaft 512. As the proximal shaft 512 is flexible, it bends appropriately in order to enter and traverse the artery 504 without causing damage.

Figure 6:
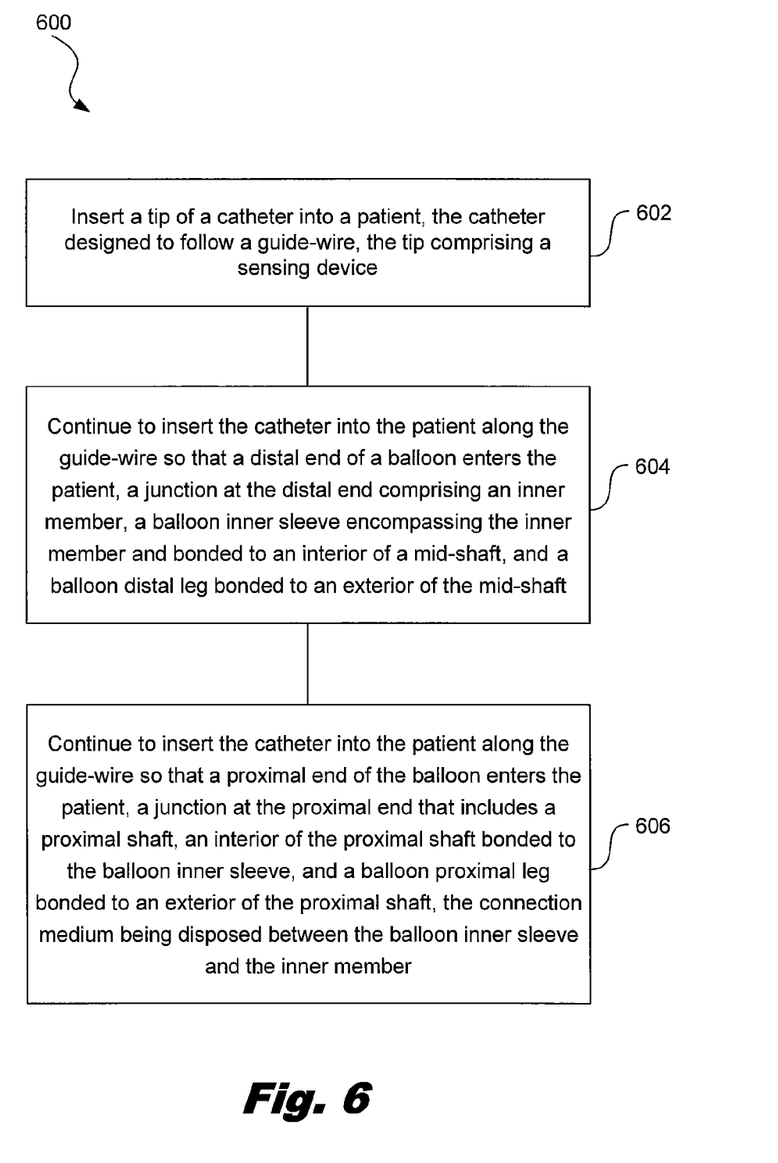
FIG. 6 is a flowchart describing an illustrative method for utilizing a therapeutic sensing catheter within a patient, according to one example of principles described herein.

FIG. 6 is a flowchart showing an illustrative method 600 for inserting a balloon catheter into a patient. According to certain illustrative examples, the method includes inserting 602 a tip of a catheter into a patient, the catheter designed to follow a guide-wire, the tip comprising a sensing device. The method further includes continuing 604 to insert the catheter into the patient along the guide-wire so that a distal end of a balloon enters the patient, a junction at the distal end comprising an inner member, a balloon inner sleeve encompassing the inner member and bonded to an interior of a mid-shaft, and a balloon distal leg bonded to an exterior of the mid-shaft. The method further includes continuing 606 to insert the catheter into the patient along the guide-wire so that a proximal end of the balloon enters the patient, a junction at the proximal end that includes a proximal shaft, an interior of the proximal shaft bonded to the balloon inner sleeve, and a balloon proximal leg bonded to an exterior of the proximal shaft, the connection medium being disposed between the balloon inner sleeve and the inner member.

Figure 7:
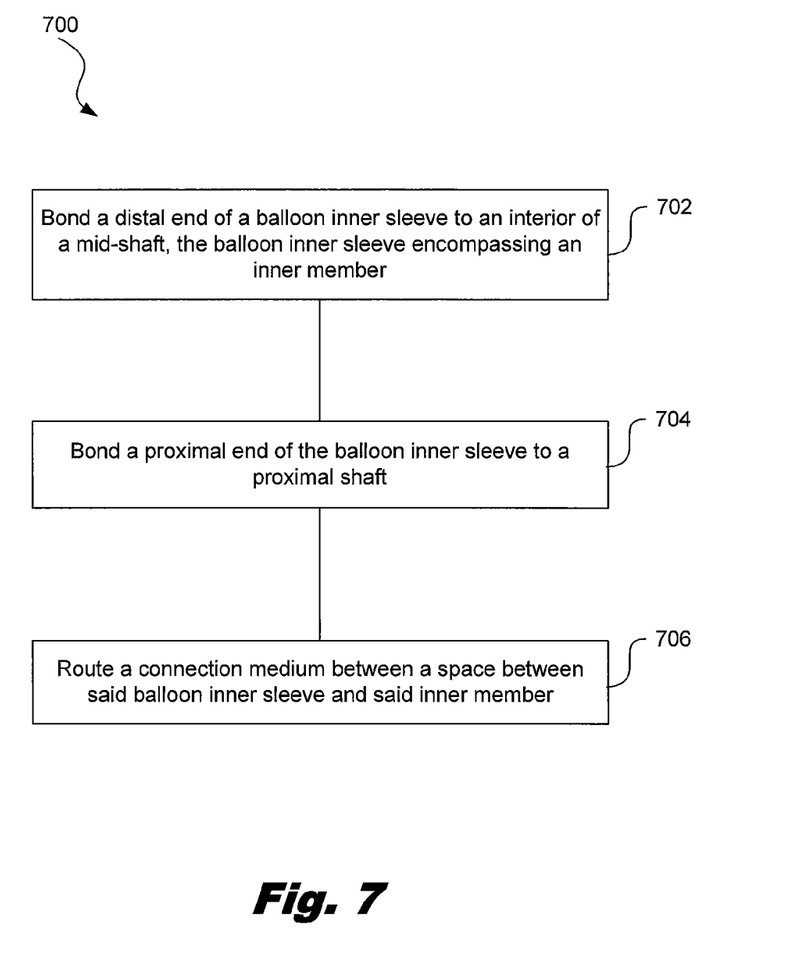
FIG. 7 is a flowchart showing an illustrative method for fabricating a sensing balloon catheter, according to one example of principles described herein.

FIG. 7 is a flowchart showing an illustrative method for fabricating a balloon catheter. According to certain illustrative examples, the method includes bonding 702 a distal end of a balloon inner sleeve to an interior of a mid-shaft, the balloon inner sleeve encompassing an inner member. The method further includes bonding 704 a proximal end of the balloon inner sleeve to a proximal shaft, and routing 706 a connection medium between a space between said balloon inner sleeve and said inner member.

Although illustrative embodiments have been shown and described, a wide range of modification, change, and substitution is contemplated in the foregoing disclosure and in some instances, some features of the present disclosure may be employed without a corresponding use of the other features. It is understood that such variations may be made in the foregoing without departing from the scope of the present disclosure. Accordingly, it is appropriate that the appended claims be construed broadly and in a manner consistent with the scope of the present disclosure.

What is claimed is:

1. A balloon catheter, comprising:
a junction on a distal end of a balloon, the junction comprising:
an inner member defining a guidewire lumen;
a balloon inner sleeve encompassing the inner member and bonded to an interior of a mid-shaft; and
a balloon distal leg bonded to an exterior of the mid-shaft;
wherein a lumen is disposed between the balloon inner sleeve and the inner member.

2. The catheter of claim 1, wherein a space defined between the balloon inner sleeve and the inner member comprises a gas.

3. The catheter of claim 1, wherein a signal-transmitting connector is allowed to move freely within the lumen.

4. The catheter of claim 1, further comprising a proximal junction comprising:
a proximal shaft, an interior of the proximal shaft bonded to the balloon inner sleeve; and
a balloon proximal leg bonded to an exterior of the proximal shaft.

5. The catheter of claim 4, wherein the proximal shaft comprises an axial dual lumen shaft.

6. The catheter of claim 5, wherein an inner lumen of the dual lumen shaft is used to pass a fluid to inflate the balloon.

7. The catheter of claim 5, wherein the balloon inner sleeve is disposed between an outer lumen of the dual lumen shaft and an inner lumen of the dual lumen shaft.

8. The catheter of claim 1, wherein the mid-shaft is independent from a proximal shaft and connects between the balloon and a sensing device.

9. The catheter of claim 1, wherein the balloon is non-compliant.

10. The catheter of claim 1, wherein a structure of the balloon inner sleeve is sufficient to protect the lumen when the balloon is inflated.

11. The catheter of claim 1, wherein the lumen comprises at least one of: an electrical conduction wire and an optical fiber.

12. The catheter of claim 1, wherein the lumen comprises an electrical conduction wire that carries data produced by a sensing device disposed adjacent the distal end of the balloon.

13. The catheter of claim 1, wherein the lumen comprises an electrical conduction wire that provides power to a sensing device at a distal end of the balloon.

14. The catheter of claim 1, wherein the lumen comprises a driveshaft lumen to drive a sensing device at a distal end of the balloon.

15. The catheter of claim 1, wherein the inner member is bonded to an interior of the mid-shaft by one of: a thermal bond and a laser bond.

16. A therapeutic catheter, comprising:
an inner member surrounded by an inner sleeve and defining a space therebetween; and
a connection medium extending within the space between the inner member and the inner sleeve, the connection medium connecting a sensing device disposed adjacent a distal end of the catheter to a proximal end of the catheter;
the catheter including a proximal shaft and a separate distal shaft, the distal shaft receiving at least a portion of the inner member, the inner sleeve and the connection medium,
wherein the inner sleeve is joined to the distal shaft at a distal end of the sleeve and the proximal shaft at a proximal end of the sleeve.

17. The catheter of claim 16, wherein the distal shaft comprises an independent mid-shaft extending between the sleeve and the sensing device.

18. The catheter of claim 17, wherein the mid-shaft is joined to the inner sleeve through one of: a laser bond and a thermal bond.

19. The catheter of claim 16, wherein the connection medium is allowed to move freely in the space, the space comprising gas.

20. The catheter of claim 19, wherein the proximal shaft comprises an axial dual lumen shaft.

21. The catheter of claim 19, wherein the inner sleeve is bonded to an outer lumen of a dual lumen shaft.

22. The catheter of claim 19, wherein an inner lumen of a dual lumen shaft is used to pass a fluid to inflate a balloon mounted circumferentially about the inner sleeve.

23. The catheter of claim 16, wherein the sensing device is one of: an ultrasound device and an optical coherence tomography device.

24. A method for forming a sensing balloon catheter, the method comprising:
   joining a distal end of a balloon inner sleeve to an interior of a mid-shaft, the balloon inner sleeve encompassing an inner member;
   joining a proximal end of the balloon inner sleeve to a proximal shaft;
   mounting a sensor adjacent the distal end of the balloon inner sleeve, the sensor having a connection medium for transmitting communication signals to a proximal end of the balloon catheter; and
   routing the connection medium through a space between the balloon inner sleeve and the inner member.

25. The method of claim 24, wherein the space between the balloon inner sleeve and the inner member comprises a gas.

26. The method of claim 24, wherein the connection medium is allowed to move freely within the space between the inner member and the balloon inner sleeve.

27. The method of claim 24, wherein joining the proximal end or joining the distal end comprises at least one of: thermal bonding and laser bonding.

28. The method of claim 24, further comprising connecting the mid-shaft to the sensor.

29. The method of claim 24, further comprising bonding a proximal end of the balloon inner sleeve to an exterior of the proximal shaft.

30. The method of claim 24 wherein the communication medium is an assembly that comprises at least one of an electrical conductor and an optical fiber.

* * * * *